US006794159B1

(12) United States Patent
Tou et al.

(10) Patent No.: US 6,794,159 B1
(45) Date of Patent: Sep. 21, 2004

(54) METHOD OF REMOVING N-TERMINAL ALANINE RESIDUES FROM POLYPEPTIDES WITH AEROMONAS AMINOPEPTIDASE

(75) Inventors: Jacob S. Tou, Ballwin, MO (US); Douglas W. Taylor, Ballwin, MO (US)

(73) Assignee: Pharmacia Corporation, Chesterfield, MO (US)

(*) Notice: Subject to any disclaimer, the term of this patent is extended or adjusted under 35 U.S.C. 154(b) by 0 days.

(21) Appl. No.: 09/541,844

(22) Filed: Apr. 3, 2000

Related U.S. Application Data

(60) Provisional application No. 60/132,062, filed on Apr. 30, 1999.

(51) Int. Cl.$^7$ .............................. C12P 21/06; C12N 9/48
(52) U.S. Cl. ...................................... 435/68.1; 435/212
(58) Field of Search ................................ 435/68.1, 212

(56) References Cited

U.S. PATENT DOCUMENTS

| | | | |
|---|---|---|---|
| 4,055,468 A | | 10/1977 | Umezawa et al. |
| 4,870,107 A | | 9/1989 | Yoshimoto et al. |
| 4,900,673 A | * | 2/1990 | Harper et al. |
| 5,013,662 A | | 5/1991 | Ben-Bassat et al. |
| 5,212,091 A | | 5/1993 | Diaz-Collier et al. |
| 5,395,763 A | | 3/1995 | Weinberg et al. |
| 5,514,483 A | | 5/1996 | Sujita et al. |
| 5,565,330 A | | 10/1996 | Atkinson et al. |
| 5,573,923 A | | 11/1996 | Atkinson et al. |
| 5,635,371 A | * | 6/1997 | Stout et al. |
| 5,763,215 A | * | 6/1998 | Blumberg et al. |
| 5,783,413 A | * | 7/1998 | Pedersen et al. |
| 6,165,746 A | * | 12/2000 | Heitzmann et al. |
| 6,444,802 B1 | | 9/2002 | Kapeller-Libermann et al. |

FOREIGN PATENT DOCUMENTS

| | | | |
|---|---|---|---|
| EP | 0204527 A1 | | 5/1986 |
| EP | 0489711 A2 | | 6/1992 |
| EP | 191827 B1 | * | 10/1992 |
| JP | 7289256 A | * | 11/1995 |
| WO | WO 8402351 A1 | | 6/1984 |
| WO | WO 8601229 A1 | | 2/1986 |
| WO | WO 9829433 A2 | | 7/1998 |

OTHER PUBLICATIONS

Prescott et al., "Aeromonas Aminopeptidaes: Purification and Some General Properties" (1996) Arch. Biochem. Biophys., 117, 328–336.*

Prescott et al., "Aeromonas Aminopeptidase. Improved Isolation and Some Physical Properties" (1971) J. Biol. Chem., 246, 1756–1764.*

Wagner et al., "Specificity of Aeromonas Aminopeptidase Toward Amino Acid Amides and Dipeptides" (1972) J. Biol. Chem., 247, 1208–1210.*

Wilkes et al., "Specificity of Aeromonas Aminopeptidase Toward Oligopeptides and Polypeptides" (1973) Eur. J. Biochem., 34, 459–466.*

Prescott et al., "Aeromonas Aminopeptidase" (1975) Methods Enzymol., 45, 530–543.*

Izawa et al., "Debittering of Protein Hydrolysates Using Aeromonas caviae Aminopeptidase" (1997) J. Agri.Food Chem., 45(3), 543–545.*

Obata et al., "Purification and Properties of an Aminopeptidase from a Protamine–Degrading Marine Bacterium" (1997) Biosci. Biotech. Biochem., 67(7), 1102–1108.*

Bachmair et al., "In Vivo Half–Life of a Protein Is a Function of Its Amino–Terminal Residue," Science 234(47):179–186, 1986.

Bayliss, M.E. et al., "Modified Activity of Aeromonas Aminopeptidase: Metal Ion Substitutions and Role of Substrates," Biochemistry 25(24):8113–8117, 1986. Cited in International Search Report.

Ben–Bassat et al., "Processing of the Initiation Methionine from Proteins: Properties of the *Escherichia coli* Methionine Aminopeptidase and Its Gene Structure," J. Bacteriology 169(2):751–757, 1987.

Berezovsky et al., "Amino acid composition of protein termini are biased in different manners," Protein Engineering 12(1):23–30, 1999.

Chicz et al., "High–Performance LIquid Chromotography: Effective Protein Purification by Various Chromatographic Modes," Methods of Enzymology, vol. 182, "Guide to Protein Purification", pp. 392–421, Edited by M. P. Deutscher, Academic Press, Inc., San Diego, CA, 1990.

Grigoryev et al., "A Mouse Amidase Specific for N–terminal Asparagine: The Gene, the Enzyme, and Their Function in the N–End Rule Pathway," J. Biol. Chem. 271(45):28521–28532, 1996.

Hermanson et al. "Activation Methods," Immobilized Affinity Ligand Techniques, 1992, pp. 51–56.

Kennedy, R.M., "Hydrophobic Chromatography," Methods of Enzymology, vol. 182, "Guide to Protein Purification", pp. 339–343, Edited by M. P. Deutscher, Academic Press, Inc., San Diego, CA, 1990.

(List continued on next page.)

*Primary Examiner*—Jon P. Weber

(57) ABSTRACT

This invention describes a method of removing N-terminal alanine residues from polypeptides, preferably recombinant proteins, using an aminopeptidase derived from the marine bacterium *Aeromonas proteolytica*. Accordingly, Aeromonas aminopeptidase (AAP; E.C. 3.4.11.10) can be used to remove N-terminal alanyl residues from derivatives of human somatotropin (hST, human growth hormone, or hGH), porcine somatotropin (pST), and bovine somatotropin (bST), for example, to yield proteins having their native amino acid sequences. The enzyme reactions can be carried out in free solution, or the AAP can be immobilized on a solid support, for reactions carried out in vitro. An efficient method for converting Ala-hGH to hGH, for example, comprises expression of Ala-hGH in *E. coli*, recovery of inclusion bodies, solubilization and refolding in detergent, detergent removal by ultrafiltration, selective precipitation, enzyme cleavage, followed by two column chromatography steps.

48 Claims, 15 Drawing Sheets

OTHER PUBLICATIONS

Kitazono, A., et a., "Isolation and characterization of the prolyl aminopeptidase gene (pap) from *Aeromonas sobria:* comparison with the Bacillus coagulans enzyme," J. Biochem (Tokyo) 116(4):818–825, Oct. 1994.

Prescott et al., "One Hundred Fold Increased Activity of *Aeromonas* Aminopeptidase by Sequential Substitutions with Ni(II) or Cu(II) Followed by Zine," Biochem. Biophys. Res. Comm. 114(2):646–652, 1983.

Rossomando, E.F., "Ion–Exchange Chromatography," Methods in Enzymology, vol. 182, "Guide to Protein Purification," pp. 309–317, Edited by M. P. Deutscher, Academic Press, Inc., San Diego, CA, 1990.

Stellwagen, E., "Gel Filtration," Methods in Enzymology, vol. 182, "Guide to Protein Purification," pp. 317–328, Edited by M.P. Deutscher, Academic Press, Inc., San Diego, CA, 1990.

Stewart et al., "The Sequence of Porcine Protein $NH_2$–terminal Asparagine Amidohydrolase; A New Component of the N–End Rule Pathway," J. Biol. Chem. 270(1):25–28, 1995.

Varshavasky, A., "The N–End Rule," Cell 69:725–735, 1992.

Varshavsky, A., "The N–end rule: Functions, mysteries, uses," Proc. Nat'l. Acad. Sci. USA 93:12142–12149, 1996.

Weinberg et al., "A chromosomal expression vector fo r*Escherichia coli* based on th bacteriophage Mu," Gene 126:25–33, 1993.

* cited by examiner

*Figure 1 - Structure of Ala-hGH and hGH*
CORRECT HUMAN GROWTH HORMONE N-TERMINAL
SEQUENCE CAN BE ACHIEVED BY THE *IN VITRO* ENZYMATIC
CLEAVAGE OF ALA-HUMAN GROWTH HORMONE
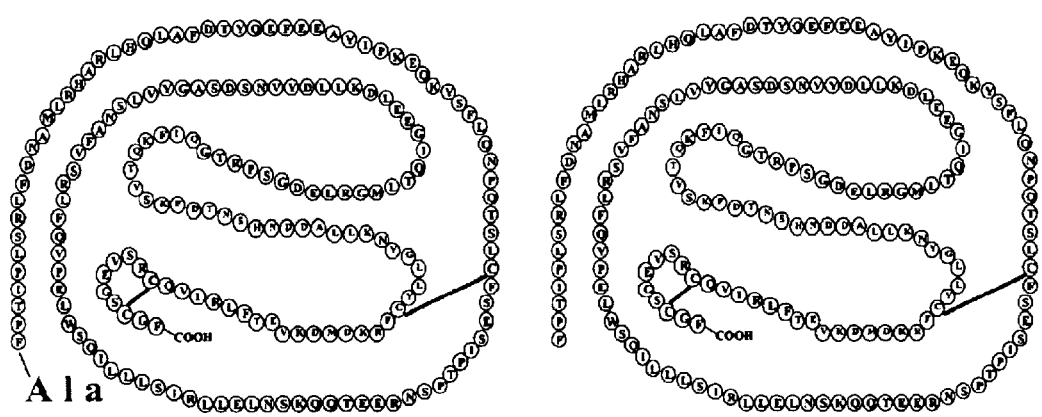

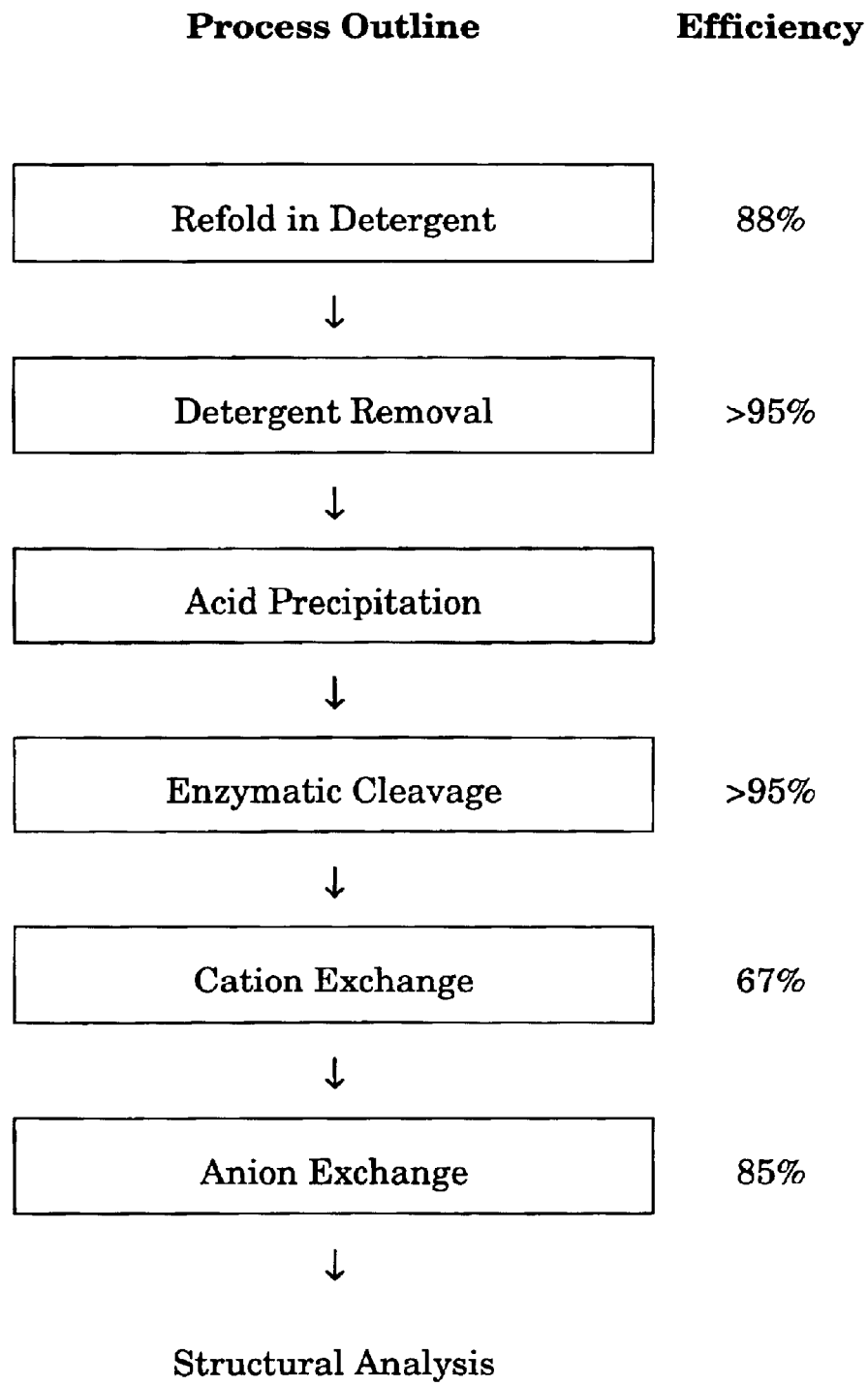
Figure 2 - Process for Production of hGH from Ala-hGH

Figure 3 - Kinetics of removal of Ala from Ala-hGH by AAP
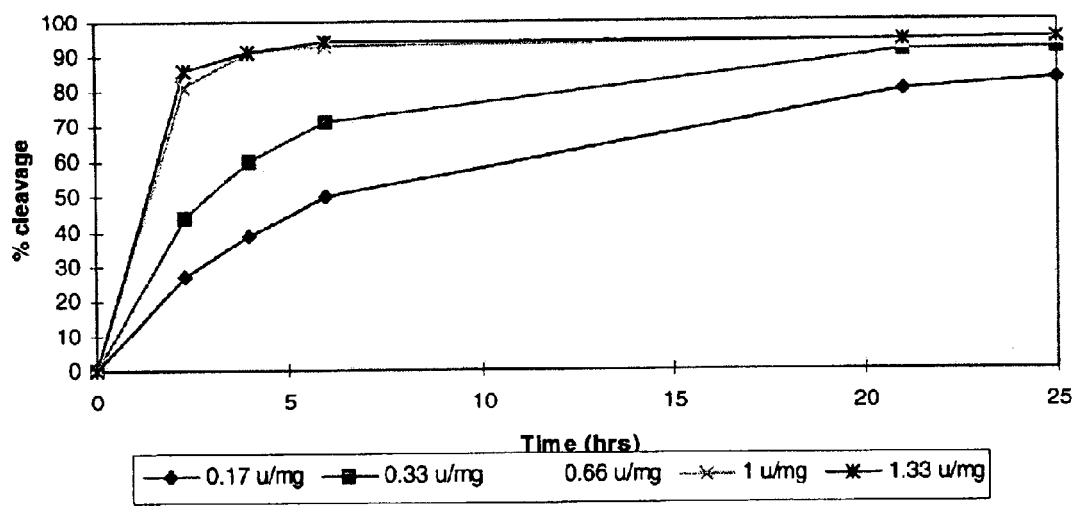
Studies of enzymatic removal of alanine from Ala-hGH: [Ala-hGH] 3 mg/ml; [AAP] 0.5, 1.0, 2.0, 3.0, and 4.0 units/ml; volume 6 ml. Cleavage efficiencies were determined by ES/MS. All reactions were performed at room temperature.

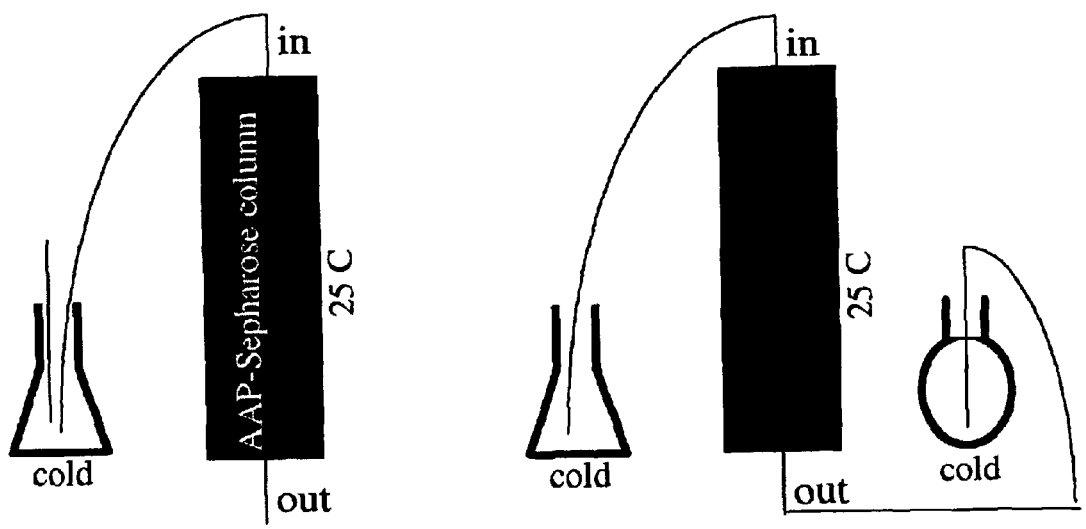
Figure 4 - Enzymatic cleavage process options - Column mode
Re-circulation mode
192 ml/hr;10 passes/24 hr
Residence time= 180 min
Flow-through mode
19.8 ml/hr; 1 pass
Residence time= 175 min

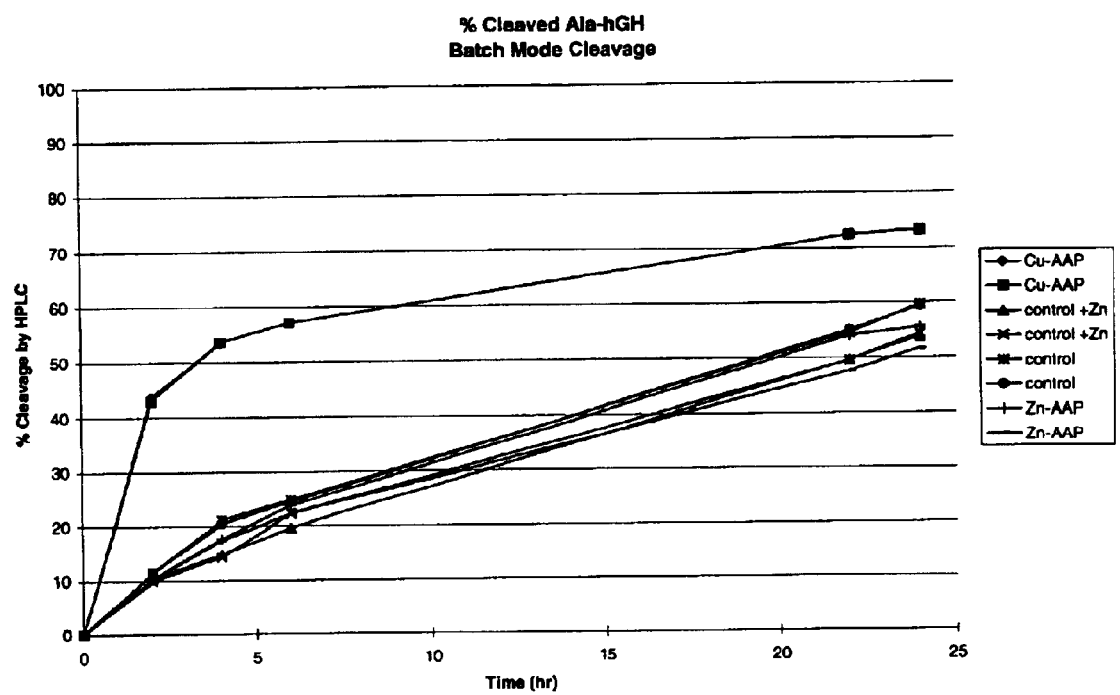
Figure 5 - Batch mode cleavage of Ala-hGH

Figure 6 - Recirculation mode cleavage of Ala-hGH
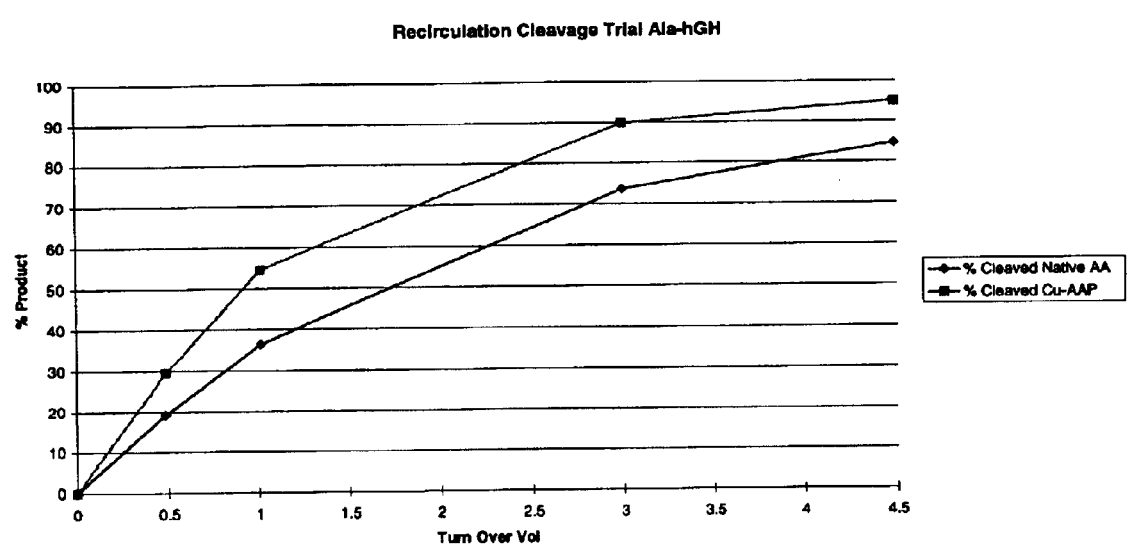

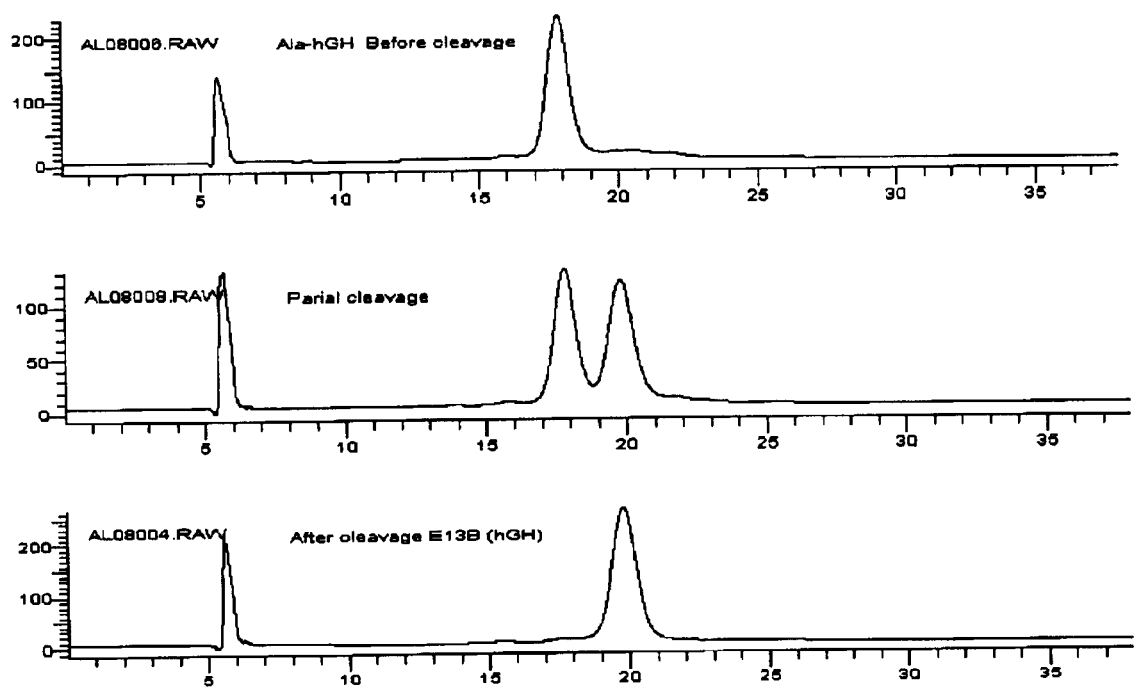
*Figure 7 - Cleavage efficiency analyzed by HPLC*

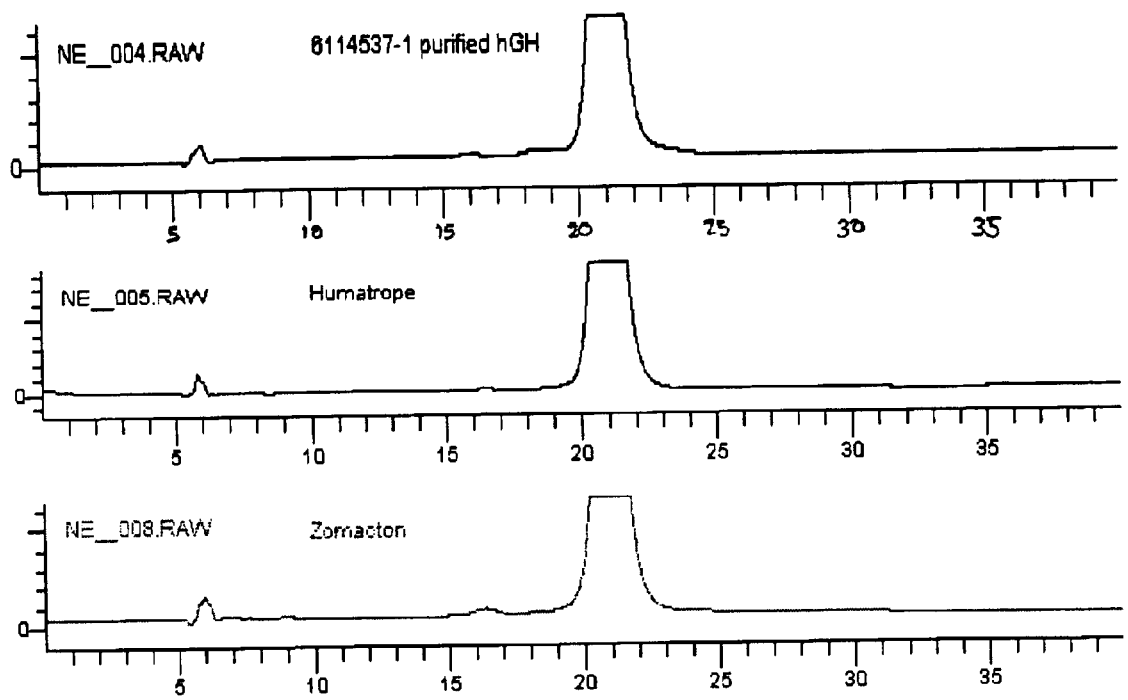
Figure 8 - Product comparison by RP-HPLC

Figure 9 - Products of Ala-hGH treated with AAP analyzed by tryptic mapping
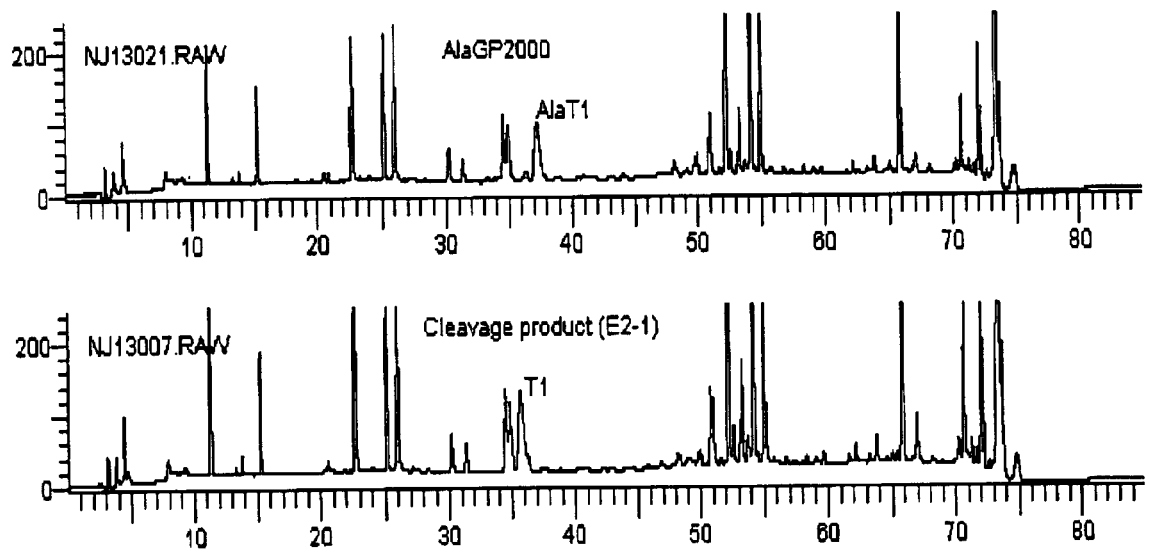
Ala-T1: N-terminal peptide from Ala-hGH (top)   (AFPTIPLSR)
T1: N-terminal peptide from hGH (bottom)   ( FPTIPLSR)

Figure 10 - Quantitative analysis of residual Ala-hGH in hGH by tryptic digest
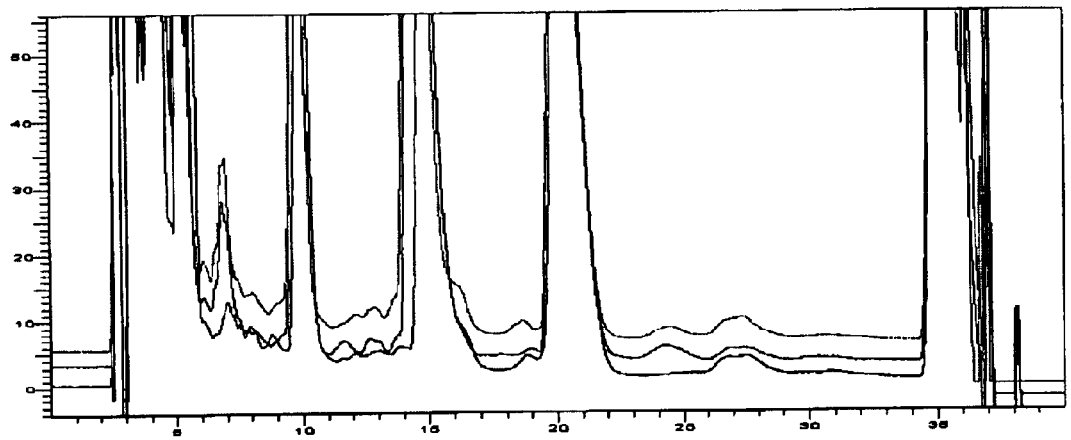
Baseline resolution of Ala-T1 and T1 peptides allows quantification of residual uncleaved Ala-hGH.

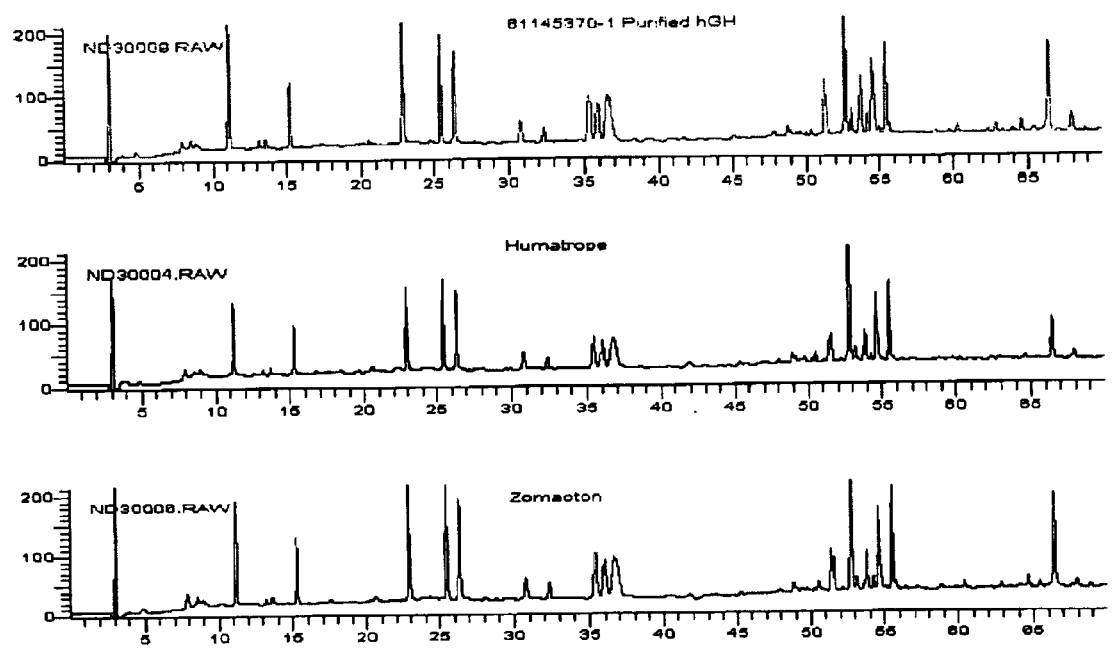
Figure 11 - Product comparison by tryptic mapping

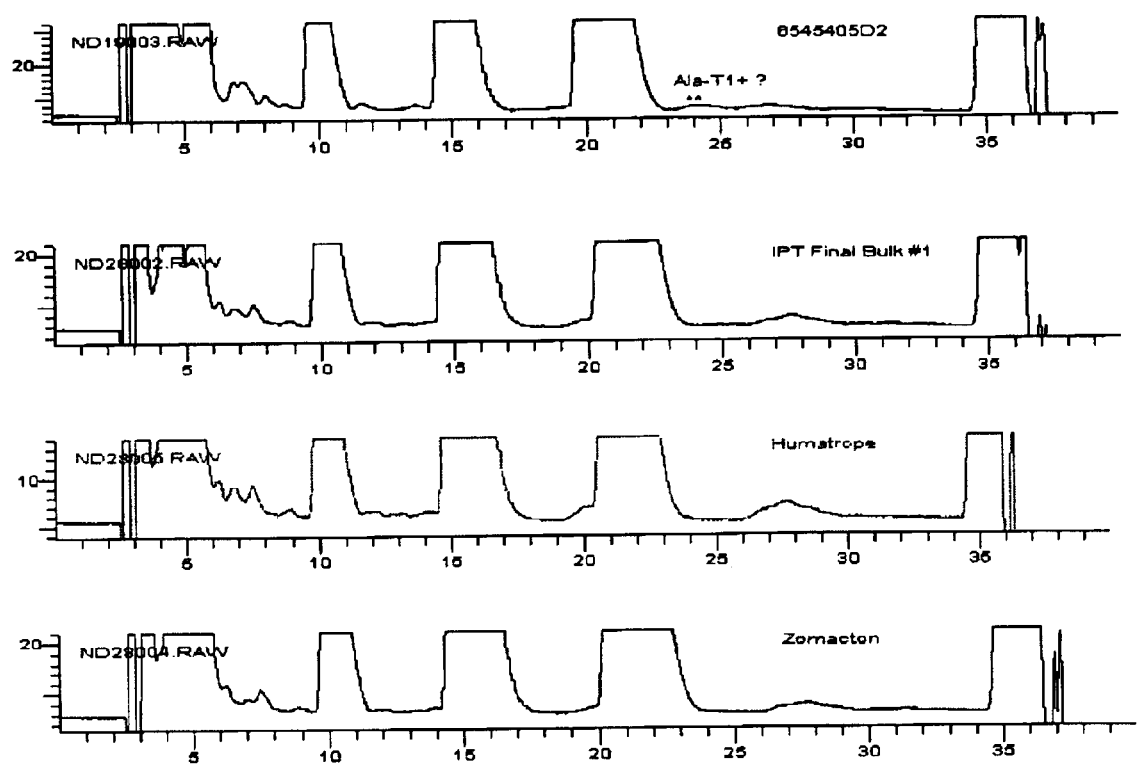
Figure 12 - Residual levels of Ala-hGH in the final product by tryptic mapping

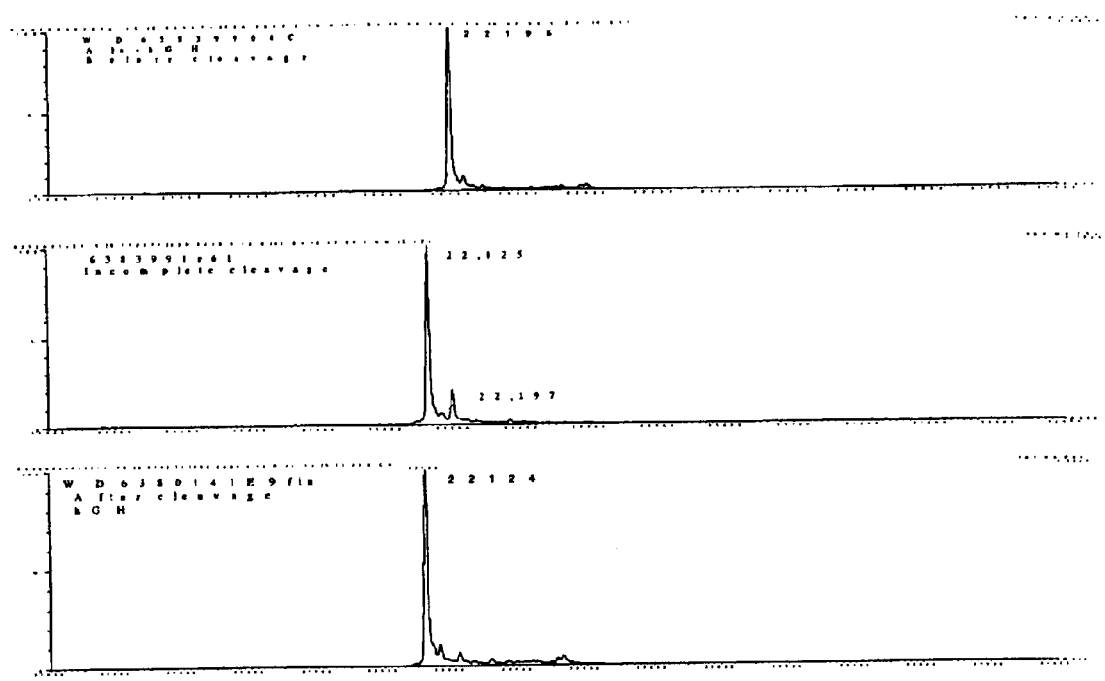
Figure 13 - Cleavage efficiency analyzed by ES/MS

*Figure 14 - Product analysis by RP-HPLC, SE-HPLC, and ES/MS*
PRODUCT ANALYSIS
Top: RP-HPLC (Vydac C18) using 65-85%/20 min acetonitrile gradient in 1% TF
Center: SE-HPLC (BioRad Bio-Sil SEC 250) using 60% acetonitrile/80 mM TFA isocratic
Bottom: ES/MS: Ala-hGH (22,198); hGH (22,125)
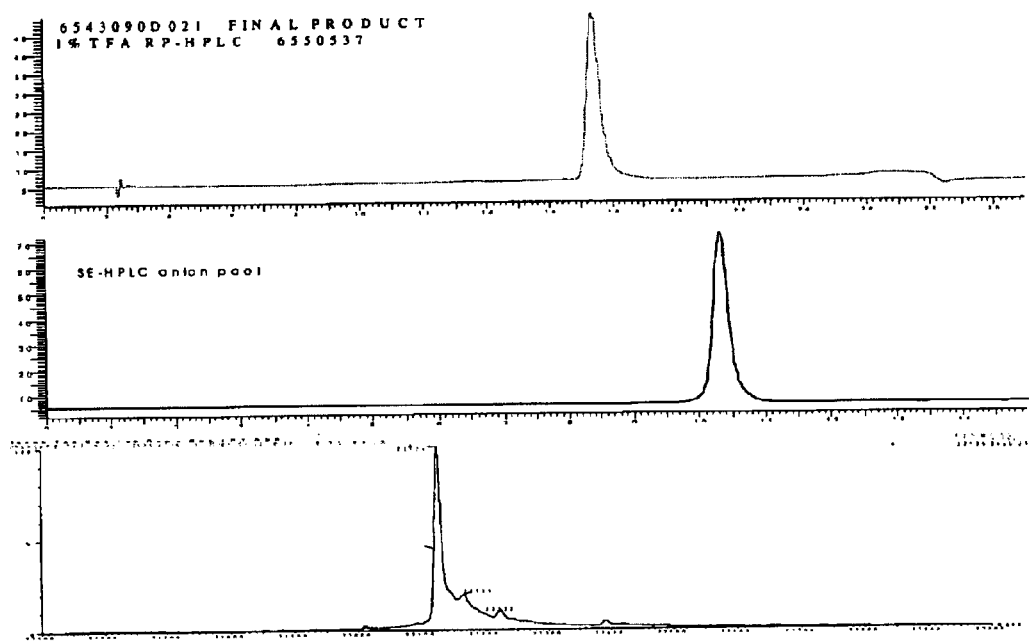

*Figure 15 - Product analyzed by N-terminal sequencing*
*In cycle 1 (left), Phe (18.3 min) is the only significant residue detected; Proline (14.2 min) is the expected residue for cycle 2 (right). The amount of alanine (\*) is negligible in both cycles indicating no Ala-hGH in the product.*
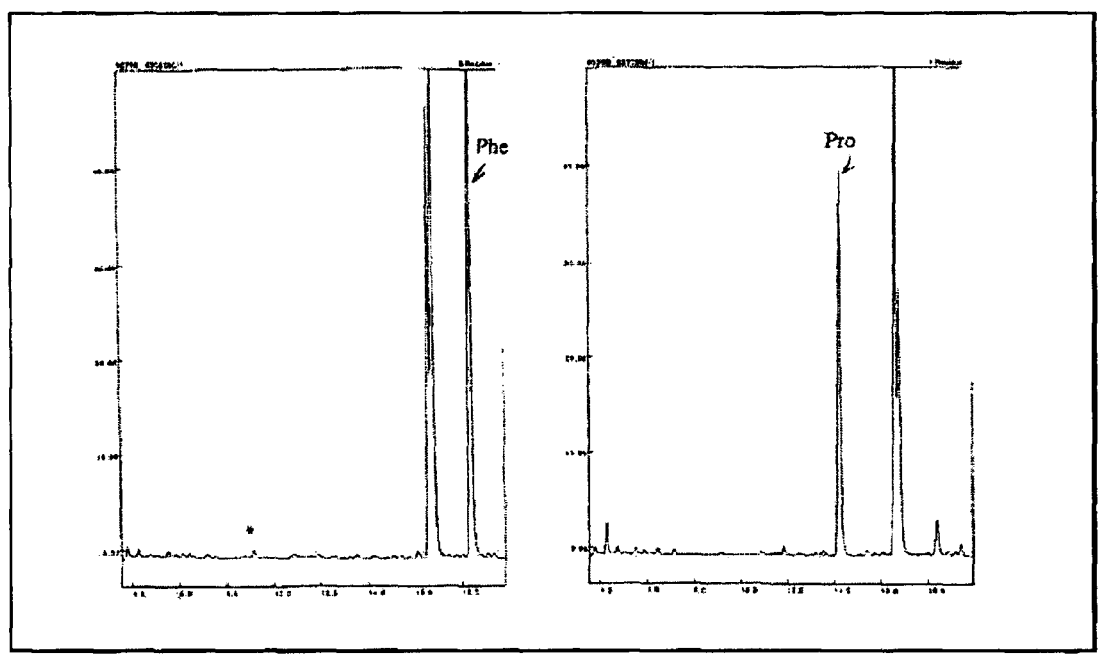

METHOD OF REMOVING N-TERMINAL ALANINE RESIDUES FROM POLYPEPTIDES WITH AEROMONAS AMINOPEPTIDASE

The present application claims priority under Title 35, United States Code, § 119 of U.S. Provisional Application Ser. No. 60/132,062, filed Apr. 30, 1999.

FIELD OF THE INVENTION

This invention describes a method of removing N-terminal alanine residues from polypeptides, preferably recombinant proteins, using an aminopeptidase derived from the marine bacterium *Aeromonas proteolytica*. Accordingly, Aeromonas aminopeptidase (AAP; E.C. 3.4.11.10) can be used to remove N-terminal alanyl residues from derivatives of human somatotropin (hST, human growth hormone, or hGH), porcine somatotropin (pST), and bovine somatotropin (bST), for example, to yield proteins having their native amino acid sequences. The enzyme reactions can be carried out in free solution, or the AAP can be immobilized on a solid support, for reactions carried out in vitro. An efficient method for converting Ala-hGH to hGH, for example, comprises expression of Ala-hGH in *E. coli*, recovery of inclusion bodies, solubilization and refolding in detergent, detergent removal by ultrafiltration, selective precipitation, enzyme cleavage, followed by two column chromatography steps.

BACKGROUND OF THE INVENTION

Recombinant proteins that mimic or have the same structure as native proteins are highly desired for use in therapeutic applications, as components in vaccines and diagnostic test kits, and as reagents for structure/function studies. Mammalian, bacterial, and insect cells are commonly used to express recombinant proteins for such applications. Bacterial expression systems, however, are often used when large quantities of protein are needed for experimental or clinical studies, and the protein is capable of being refolded to its proper conformation. Bacterial systems, in particular, offer significant cost advantages over other expression vector systems when eukaryotic post-translational modifications (e.g., glycosylation) are not required, or desired, in the final protein product.

Recombinant proteins expressed in bacteria, such as *E. coli*, are often sequestered into insoluble inclusion bodies. Heterologous proteins harvested from inclusion bodies often retain an additional amino acid residue such as methionine at their amino terminus. This methionine residue (encoded by the ATG start codon) is often not present, however, on native or recombinant proteins harvested from eukaryotic host cells. The amino termini of many proteins made in the cytoplasm of *E. coli*, however, are processed by enzymes, such as methionine aminopeptidase (Ben Bassat et al., *J. Bacteriol.* 169: 751–757, 1987), so that upon expression the methionine is ordinarily cleaved off the N-terminus.

The amino acid composition of protein termini are biased in many different manners (Berezovsky et al., *Protein Engineering* 12(1): 23–30, 1999). Systematic examination of N-exopeptidase activities led to the discovery of the 'N-terminal'-or 'N-end rule': the N-terminal (f)Met is cleaved if the next amino acid is Ala, Cys, Gly, Pro, Ser, Thr, or Val. If this next amino acid is Arg, Asp, Asn, Glu, Gln, Ile, Leu, Lys or Met, the initial (f)Met remains as the first amino acid of the mature protein. The radii of hydration of the amino acid side chains was proposed as physical basis for these observations (Bachmain et al., *Science*, 234: 179–186, 1986; Varshavsky, *Cell*, 69: 725–735, 1992). The half-life of a protein (from 3 min to 20 hours), is dramatically influenced by the chemical structure of the N-terminal amino acid (Stewart et al., *J. Biol. Chem.*, 270: 25–28, 1995; Griegoryev et al.,*J. Biol., Chem.*, 271: 28521–28532, 1996). Site-directed mutagenesis was subsequently used to confirm the 'N-end rule' by monitoring the life-span of recombinant proteins containing altered N-terminal amino acid sequences (Varshavsky, *Proc. Natl. Acad. Sci. USA*, 93: 12142–12149, 1996). A statistical analysis of the amino acid sequences at the amino termini of proteins suggested that Met and Ala residues are over-represented at the first position, whereas at positions +2 and +5, Thr is preferred (Berezovsky et al., *Protein Engineering* 12(1): 23–30, 1999). C terminal biases, however, show a preference for charged amino acids and Cys residues (Berezovsky et al., *Protein Engineering*, 12(1): 23–30, 1999).

Recombinant proteins that retain the N-terminal methionine, in some cases, have biological characteristics that differ from the native species lacking the N-terminal methionine. Human growth hormone that retains its N-terminal methionine (Met-hHG), for example, can promote the induction of undesireable antibodies, compared to hGH purified from natural sources or recombinant hGH that is prepared in such a way that has the same primary sequence as native hGH (lacking an N-terminal methionine). Low-cost methods of generating recombinant proteins that mimic the structure of native proteins are often highly desired for therapeutic applications (Sandman et al., *Bio/Technology* 13:504–6 (1995)).

One method of preparing native proteins in bacteria is to express the desired protein as part of a larger fusion protein containing a recognition site for an endoprotease that specifically cleaves upstream from the start of the native amino acid sequences. The recognition and cleavage sites can be those recognized by native signal peptidases, which specifically clip the signal peptide of the N-terminal end of a protein targeted for delivery to a membrane or for secretion from the cell. In other cases, recognition and cleavage sites can be engineered into the gene encoding a fusion protein so that recombinant protein is susceptible to other non-native endoproteases in vitro or in vivo. The blood clotting factor Xa, collagenase, and the enzyme enterokinase, for example, can be used to release different fusion tags from a variety of proteins. Economic considerations, however, generally preclude use of endoproteases on a large scale for pharmaceutical use.

Another method of preparing native proteins in bacteria is to use the enzyme methionine aminopeptidase (MAP) to process the N-terminal methionine from *E. coli*-derived recombinant proteins. Met-hGH, for example, can be treated with MAP to generate hGH. U.S. Pat. Nos. 4,870,017 and 5,013,662 describe the cloning, expression, and use of *E. coli* methionine aminopeptidase to remove Met from a variety of peptides and Met-IL-2. The ability to release amino acids from a variety of peptide substrates was analyzed, revealing that MAP cleaves only N-terminal methionine on peptides that are at least three amino acids long. The nature of amino acids in the second and third positions also appear to be significant. Methionine was released, for example, from Met-Ala-Met; Met-Gly-Met, Met-Ala-Pro-Thr-Ser-Ser-Ser-Thr-Lys-Lys-Thr-Gln-Leu (SEQ ID NO: 1), and Met-Pro-Thr-Ser-Ser-Ser-Thr-Lys-Lys-Gln-Cys (SEQ ID NO: 2), but not Met-Phe-Gly, Met-Leu-Phe, Met-Met-Met, among others. No amino acids were released from Leu-Ala-Pro-Thr-Ser-Ser-Ser-Thr-Lys-Lys-Thr-Gln-Leu (SEQ ID NO: 3), Ala-Pro-Thr-Ser-Ser-Ser- Thr-Lys-Lys-Thr-Gln-Leu (SEQ ID NO: 4), or Pro-Thr-Ser-Ser-Ser-Thr-Lys-Lys-Gln-Cys (SEQ ID NO: 5).

WO 84/02351 discloses a process for preparing ripe (native) proteins such as human growth hormone or human proinsulin from fusion proteins using leucine aminopeptidase. A fusion protein having the amino acid sequence $(Y_m \ldots Y_2Y_1)$-$(Pro)_p$-$(X_1X_2 \ldots X_n)$ in which the $(Y_m \ldots Y_2Y_1)$-$(Pro)_p$ is the pro-sequence and the rest is the ripe protein, m is an integer greater than 2, Y is an arbitrary amino acid, p is 0, if $X_1$ or $X_2$ is Pro, and 1 if X, or $X_1$ is different from Pro, X is an arbitrary amino acid, and n is an integer greater than or equal to 4, is converted by stepwise cleavage with aminopeptidase removing amino acids $Y_m \ldots Y_2$ if p=1 or $X_1$=Pro, or the groups $Y_m \ldots Y_2$-$Y_1$ if $X_2$=Pro and then the two amino acids $Y_1$-Pro if p=1 are cleaved off enzymatically in one or two steps in a manner known per se, and similarly $Y_1$ alone is cleaved off, if $X_1$=Pro.

European Patent Application EP 0 204 527 A1 discloses a method of removing the N terminal methionine from proteins of the formula H-Met-X-Pro-Y-OH to yield a protein represented by the formula H-X-Pro-Y-OH, where X is an amino acid other than proline and Y is a peptide chain. Aminopeptidase M was preferred, but leucine aminopeptidase, aminopeptidase PO, or aminopeptidase P could also be used. The N-terminal methionine was removed from derivatives of human interleukin-2 and human growth hormone.

Aeromonas aminopeptidase (AAP), an exo-peptidase isolated from the marine bacterium *Aeromonas proteolytica*, can also be used to facilitate the release of N-terminal amino acids from peptides and proteins (Wilkes et al., *Eur. J. Biochem.* 34(3), 459–66, 1973). The most favorable sequence is X-//-Y- whereas Y is a hydrophobic residue, preferably an aromatic amino acid, such as phenylalanine. Residues susceptible to hydrolysis include all hydrophobic, aromatic, and basic amino acids, plus proline. Aspartyl, glutamyl, and cysteic acid residues were not removed from the amino terminus of any substrate tested, even at high enzyme concentrations. Asparagine, glutamine, and aminoethylated cysteine, however, were released from oligopeptide substrates. Glycine was generally resistant to hydrolysis, but was slowly released from some substrates, depending on the adjacent residues. The activity of AAP on peptide substrates can also be enhanced by changing the counter metal ions, such as $Cu^{2+}$ and $Ni^{2+}$ for free enzyme AAP (Prescott et al., *Biochem. Biophys. Res. Comm.* 114(2): 646–652, 1983). AAP is a 29.5 kDa metalloenzyme containing two disulfide bonds.

European patent EP 0191827 B1 and U.S. Pat. No. 5,763,215 describe the sequential removal of N-terminal amino acids from analogs of eukaryotic proteins, formed in a foreign host, by use of Aeromonas aminopeptidase. When 8 mg methionyl-human growth hormone (Met-hGH) (dissolved in 1 mL pH 9.5 10 mM Na borate buffer) was mixed with Aeromonas aminopeptidase (dissolved at 0.4725 mg/mL in pH 9.5 Tris buffer) at a ratio of 900 to 19 and incubated at 37° C., methionine cleavage was complete in 15 min. Cleavage of the new N-terminal amino acid leucine, was slight after 22 h. The N-terminal methionine from Met-pST, Met-Interferon, Met-IGF-1, Met-interleukin-2 (Met-IL-2), and Met-Apolipoprotein E were removed by AAP. An N-terminal alanine, however, was not removed from mature superoxide dismutase.

More complicated methods can also be used to generate recombinant proteins with a native amino terminus. U.S. Pat. No. 5,783,413, for example, describes the simultaneous or sequential use of (a) one or more aminopeptidases, (b) glutamine cyclotransferase, and (c) pyroglutamine aminopeptidase to treat amino-terminally-extended proteins of the formula $NH_2$-A-glutamine-Protein-COOH to produce a desired native protein. The first aminopeptidase(s) (selected from the group consisting of dipeptidylaminopeptidase I, Aeromonas aminopeptidase, aminopeptidase P, and proline aminopeptidase), catalyze the removal of residues amino-terminal to the glutamine. The glutamine cyclotransferase catalyzes the conversion of the glutamine to pyroglutamine, and the pyroglutamine aminopeptidase catalyzes the removal of pyroglutamine to produce the desired protein product.

U.S. Pat. Nos. 5,565,330 and 5,573,923 disclose methods of removing dipeptides from the amino-terminus of precursor polypeptides involving treatment of the precursor with dipetidylaminopeptidase (dDAP) from the slime mold *Dictostelium descoideum*, which has a mass of about 225 kDa and a pH optimum of about 3.5. Precursors of human insulin, analogues of human insulin, and human growth hormone containing dipeptide extensions were processed by dDAP when the dDAP was in free solution and when it was immobilized on a suitable solid support surface.

More efficient strategies to process amino acids from the amino terminus of recombinant proteins are desirable to reduce the cost of generating therapeutic proteins that mimic the structure of native proteins. Methods that increase the levels of expression or facilitate the downstream processing of recombinant proteins will also accelerate the selection and development of small chemical molecules and other protein-based molecules destined for large scale clinical trials.

SUMMARY OF THE INVENTION

It is an object of the invention is to describe a method of removing an N-terminal alanyl group from a recombinant protein which comprises contacting said recombinant protein with Aeromonas aminopeptidase such that said N-terminal alanyl group is removed and recovering the resulting recombinant protein.

Preferably, the recombinant protein is of eukaryotic origin. Even more preferably, the recombinant protein is selected from the group consisting of human growth hormone (hGH), bovine somatotropin (bST), porcine somatotropin (pST), and human tissue factor pathway inhibitor (TFPI). Most preferably, the recombinant protein is hGH.

Preferably, the contacting process is carried out at a pH from about pH 7 to about pH 11. Even more preferably, the contacting process is carried out at a pH from about pH 8 to about pH 10. Most preferably, the contacting process is carried out at a pH of about pH 8.0 to about pH 9.5.

Preferably, the contacting process is carried out in the presence of a buffer selected from the group consisting of borate, CHES, sodium bicarbonate, sodium phosphate, and Tris-HCl. More preferably, the buffer is borate, phosphate, or Tris-HCl.

Preferably, the contacting process can be carried out wherein the aminopeptidase is immobilized. Preferably, the aminopeptidase is immobilized on a chromatography resin, chromatography surface, or chromatography gel.

Preferably, the recombinant protein is passed through a column containing the aminopeptidase immobilized on a chromatography resin.

Alternatively, the contacting process can be carried out wherein the aminopeptidase is not immobilized (e.g., in free solution).

It is also conceivable that Aeromonas aminopeptidase may permit the processing of proteins containing two or more closely-spaced alanyl residues in the N-terminal regions of polypeptides. The aminopeptidase may proceed sequentially from the N-terminus of the polypeptide or perhaps recognize additional alanine residues within a short distance of exposed N-terminal polypeptide residues. Elucidation of a consensus sequence for the alanyl-specific recognition and cleavage sites can be evaluated on a variety of protein and peptide substrates.

Aeromonas aminopeptidase may also facilitate the processing of non-alanyl residues in the N-terminal regions of proteins under the conditions disclosed in this application. Elucidation of a consensus sequence for the recognition and cleavage of these sites can be evaluated on a variety of protein and peptide substrates.

It is another object of the invention is to describe a method of removing amino-terminal amino acids from a precursor polypeptide of the formula X-Y-Pro-Z with Aeromonas aminopeptidase to yield a polypeptide of the formula Y-Pro-Z, wherein X is one or more amino acids except proline, Y is any amino acid except proline, and Z is one or more amino acids.

Preferably, X is alanine.

Preferably, Y is selected from the group consisting of phenylalanine, methionine, threonine, and aspartic acid. More preferably, Y is phenylalanine.

Most preferably, X is alanine and Y is phenylalanine.

Preferably, the precursor polypeptide is Ala-hGH.

DEFINITIONS

The following is a list of abbreviations and the corresponding meanings as used interchangeably herein:

g=gram(s)
HPLC=high performance liquid chromatography
kb=kilobase(s)
mb=megabase(s)
mg=milligram(s)
ml, mL=milliliter(s)
RP-HPLC=reverse phase high performance liquid chromatography
ug, μg=microgram(s)
ul, uL, μl, μL=microliter(s)

The following is a list of definitions of various terms and the corresponding meanings as used interchangeably herein:

The terms "aap" and "AAP" mean Aeromonas aminopeptidase.

The terms "ap" and "AP" mean aminopeptidase.

The term "amino acid(s)" means all naturally occurring L-amino acids, including norleucine, norvaline, homocysteine, and ornithine.

The term "fusion molecule" means a protein-encoding molecule or fragment thereof that upon expression, produces a fusion protein.

The term "fusion protein" means a protein or fragment thereof that comprises one or more additional peptide regions not derived from that protein.

The term "promoter" is used in an expansive sense to refer to the regulatory sequence(s) that control mRNA production.

The term "protein fragment" means a peptide or polypeptide molecule whose amino acid sequence comprises a subset of the amino acid sequence of that protein.

The term "protein molecule/peptide molecule" means any molecule that comprises five or more amino acids.

The term "recombinant" means any agent (e.g., DNA, peptide, etc.), that is, or results from, however indirectly, human manipulation of a nucleic acid molecule.

The term "specifically bind" means that the binding of an antibody or peptide is not competitively inhibited by the presence of non-related molecules.

The term "substantially-purified" means that one or more molecules that are or may be present in a naturally-occurring preparation containing the target molecule will have been removed or reduced in concentration.

BRIEF DESCRIPTION OF THE FIGURES

FIG. 1—Structure of Ala-hGH and hGH

Human growth hormone (right) (SEQ ID NO: 8) is a single-chain polypeptide (22 kDa) with four cysteine residues involved in two disulfide bond linkages. The correct N-terminal sequence can be achieved by the in-vitro enzymatic cleavage of Ala-hGH (left) (SEQ ID NO: 9) with Aeromonas aminopeptidase.

FIG. 2—Process for Production of hGH from Ala-hGH

A general process for the purification of hGH from Ala-hGH involves purification of Ala-hGH from bacterial inclusion bodies, refolding of Ala-hGH in detergent, detergent removal, acid precipitation, treatment with aminopeptidase, and purification of the native hGH by cation and anion exchange column chromatography.

FIG. 3—Kinetics of Removal of Ala from Ala-hGH by AAP

The kinetics of removal of Ala from Ala-hGH by AAP are illustrated in FIG. 3. Ala-hGH was present at 3 mg/ml and AAP at was present at 0.5, 1.0, 2.0, 3.0, and 4.0 units/ml in a total volume of 6 ml. The reactions were performed at room temperature and samples collected up through 25 hours and the products analyzed by ES/MS. Most of the reactions for the three highest concentrations of AAP were complete by 6 hours.

FIG. 4—Enzymatic Cleavage Process Options—Column Mode

A schematic comparison of steady-flow and continuous-flow cleavage process modes are illustrated.

FIG. 5—Batch Mode Cleavage of Ala-hGH

FIG. 5 illustrates a time course of enhanced cleavage of Ala-hGH by Cu-AAP compared to Zn-AAP in batch mode.

FIG. 6—Recirculation Mode Cleavage of Ala-hGH

FIG. 6 illustrates a time course of Ala-hGH by Cu-AAP compared to Zn-AAP carried out in column recirculation mode.

FIG. 7—Cleavage Efficiency Analyzed by HPLC

FIG. 7 illustrates HPLC profiles of Ala-hGH before cleavage with AAP, incomplete cleavage, and after the reaction is complete.

FIG. 8—Product Comparison by RP-HPLC

FIG. 8 illustrates the HPLC profile of hGH prepared by treating Ala-hGH with AAP, and two commercial preparations of hGH (Humatrope and Zomacton).

FIG. 9—Products of Ala-hGH Treated with AAP Analyzed by Tryptic Mapping

FIGS. 9–12 illustrate typical tryptic map profiles. FIG. 9 illustrates the profile tracings illustrating the difference in mobility of the Ala-T1 peptide compared to the T1 peptide.

FIG. 10—Quantitative Analysis of Residual Ala-hGH in hGH by Tryptic Digest

FIG. 10 shows a vertically expanded profile tracing, illustrating the differences in peak areas under the elution positions for Ala-T1 and T1.

FIG. 11—Product Comparison by Tryptic Mapping

FIG. 11 illustrates the tryptic maps of hGH purified after treatment of Ala-hGH with AAP compared to tryptic maps of hGH from commercial sources (Humatrope and Zomacton).

FIG. 12—Residual Levels of Ala-hGH in the Final Product by Tryptic Mapping

FIG. 12 shows a vertically expanded profile tracing illustrating the presence or absence of Ala-T1 in a crude preparation of hGH, the final bulk preparation of hGH, and hGH from two commercial sources (Humatrope and Zomacton).

FIG. 13—Cleavage Efficiency Analyzed by ES/MS

FIG. 13 illustrates ES/MS profiles of Ala-hGH before cleavage with AAP, incomplete cleavage, and after the reaction is complete. FIG. 8 illustrates the HPLC profile of hGH prepared by treating Ala-hGH with AAP, and two commercial preparations of hGH (Humatrope and Zomacton).

FIG. 14—Product Analysis by RP-HPLC, SE-HPLC, and ES/MS

FIG. 14 illustrates a superimposed ES/MS profile of Ala-hGH and hGH (bottom panel) along with HPLC tracings of the final product resolved on RP-HPLC and SE-HPLC columns.

FIG. 15—Product Analyzed by N-terminal Sequencing

FIG. 15 illustrates tracings of the products released after cycle 1 and cycle 2 from an automated protein sequencer. Phenylalanine (18.3 min) is the only significant residue detected after one cycle (left panel). Proline (14.2 min) is the only significant residue detected in cycle 2. The amount of alanine (*) is negligible in both cycles, indicating lack of N-terminal alanine residues in the final purified product.

DETAILED DESCRIPTION OF THE INVENTION

The following examples will illustrate the invention in greater detail, although it will be understood that the invention is not limited to these specific examples. Various other examples will be apparent to the person skilled in the art after reading the present disclosure without departing from the spirit and scope of the invention. It is intended that all such other examples be included within the scope of the appended claims.

General Methods

General methods of cloning, expressing, and characterizing proteins are found in T. Maniatis, et al., *Molecular Cloning, A Laboratory Manual*, Cold Spring Harbor Laboratory, 1982, and references cited therein, incorporated herein by reference; and in J. Sambrook, et al., *Molecular Cloning, A Laboratory Manual*, 2$^{nd}$ edition, Cold Spring Harbor Laboratory, 1989, and references cited therein, incorporated herein by reference. General and specific conditions and procedures for the construction, manipulation and isolation of antibodies are well known in the art (see, for example, Harlow and Lane, *In Antibodies: A Laboratory Manual*, Cold Spring Harbor Press, Cold Spring Harbor, N.Y. (1988)).

Reagents

Aeromonas aminopeptidase and all specialty chemicals, unless noted otherwise, were obtained from Sigma Chemical Company (St. Louis, Mo.).

Humatrope was obtained from Eli Lilly. Zomacton was obtained from Gentechnisch.

Protein Purification

Protein purification can be accomplished using any of a variety of chromatographic methods such as: ion exchange, gel filtration, hydrophobic chromatography, or reversed phase HPLC. These and other protein purification methods are described in detail in Methods in Enzymology, Volume 182 "Guide to Protein Purification" edited by Murray Deutscher, Academic Press, San Diego, Calif., 1990. Folded proteins can also be affinity-purified using affinity reagents such as monoclonal antibodies or receptor subunits attached to a suitable matrix.

Purified proteins can be analyzed by RP-HPLC, electrospray mass spectrometry, and SDS-PAGE. Protein quantitation is accomplished by amino acid composition, RP-HPLC, and Bradford protein determination techniques. Tryptic peptide mapping, performed in conjunction with electrospray mass spectrometry, can also be used to confirm the identity of proteins.

EXAMPLE 1

Preparation of Alanyl-human Growth Hormone (Ala-hGH)

Ala-hGH (FIG. 1) was expressed in *E. coli* using mini-Mu-based chromosomal expression system (Weinberg et al., *Gene* 126: 25–33, 1993; U.S. Pat. Nos. 5,395,763 and 5,514,483; U.S. patent application Ser. No. 09/044,369, filed Mar. 19, 1998, each herein specifically incorporated by reference). Ala-hGH was expressed at levels of about 1.5 to about 2.0 g/liter.

Ala-hGH was purified, refolded, and processed to a purity of >90% based on analysis of Ala-hGH (by RP-HPLC) and total protein concentration (by absorbance at $A_{280}$). Briefly, inclusion bodies were isolated and Ala-hGH was purified and refolded using methods described previously (WO 98/29433). Refolding was most commonly achieved with a >85% yield at pH 10 using as acyl-glutamate as a detergent. The detergent was then removed from the refold mixture by exhaustive ultrafiltration (10 TOVs) against pH 10 water. This was followed by an acid precipitation step to remove most of the recombinant *E. coli* proteins. The average recovery of Ala-hGH from this precipitation step was ~80–85%. This semi-purified Ala-hGH was diafiltered against the cleavage buffer (10 mM phosphate, pH 8.0) before being treated with the enzyme, preferably in an immobilized mode. After the enzymatic cleavage step, hGH was further purified by ion exchange chromatography to bulk powder. A general process outline is illustrated in FIG. 2.

EXAMPLE 2

In-vitro Processing of Ala-human Growth Hormone (Ala-hGH) with Aeromonas aminopeptidase in Free Solution Prior to the cleavage step, Ala-hGH was adjusted to 3 mg per ml concentration in 10 mM borate, pH 9.5. To this, Aeromonas aminopeptidase was added in 3 units per ml and the reaction was allowed to proceed for 24–36 hours at ambient temperature or at a shorter time at 370° C. The progress of the cleavage reaction can be monitored by RP-HPLC or by amino acid analysis of the release of alanine from Ala-hGH. At the end of reaction, the solution was quenched by adding 2% acetic acid (1:1.5 dilution w/w).

The kinetics of removal of Ala from Ala-hGH by AAP are illustrated in FIG. 3. Ala-hGH was present at 3 mg/ml and AAP at was present at 0.5, 1.0, 2.0, 3.0, and 4.0 units/ml in a total volume of 6 ml. The reactions were performed at room temperature and samples collected up through 25 hours and the products analyzed by ES/MS. Most of the reactions for the three highest concentrations of AAP were complete by 6 hours.

EXAMPLE 3

In-vitro Processing of Ala-human Growth Hormone (Ala-hGH) Using Immobilized Aminopeptidase Preparation of Immobilized Aminopeptidase Aeromonas aminopeptidase (AAP) was coupled onto resins such as Sepharose 4B resin via the cyanogen bromide (CNBr) chemistry. Commercial CNBr-activated Sepharose 4B resin was washed exhaustively with cold water and then suspended in 0.1 M sodium carbonate buffer, pH 8.5 or 10 mM phosphate, pH 8. AAP was added (100 units per gram of resin) and the mixture was gently agitated at 4° C. for overnight. After washing with water, the resin was capped with ethanolamine (0.5–1 M) at room temperature for two hours. Resin was then washed with water and equilibrated with the enzyme cleavage buffer, such as 10 mM phosphate, pH 8. The activity of this immobilized enzyme was measured by the standard assay, suggested by Sigma, using L-leucine-p-nitroanilide as a substrate. The average activity was typically 10–20 units per ml of resin bed.

In-vitro Cleavage of Ala-human Growth Hormone (hGH)

Batch Mode:

Immobilized aminopeptidase was suspended as 1:1 mix in borate or phosphate buffer. To a 7-ml tube containing 5 ml Ala-hGH in phosphate or borate buffer, one ml resin was added. This gave a total of 6 ml with 3 mg/ml protein concentration. The mixture was rocked for 10–24 hours at 20–40° C. At the end of reaction, resin was filtered off and the resulting solution was analyzed by RP-HPLC. The remaining of the solution was centrifuged using a CentriCon micro-filtration device. The filtrate was analyzed by the amino acid analyzer for the releasing of alanine. The retentate was exchanged 4–5 times with 2% acetic acid before being dried down to powder for mass spectrometry analysis.

Table 1 illustrates the effect of temperature on batch mode cleavage of Ala-hGH using immobilized AAP. The reaction is accelerated at ambient temperatures, and essentially complete beyond 54 hours.

TABLE 1

Effect of temperature on batch mode cleavage of Ala-hGH using immobilized AAP

| Temperature | Time, hrs | % cleavage |
|---|---|---|
| 4–6° C. | 16 | 48 |
|  | 54 | 65 |
|  | 89 | 75 |
| Ambient | 16 | 82 |
|  | 54 | >97 |
|  | 89 | >97 |

Circulation Mode:

Ala-hGH in 10 mM borate, pH 9.5 or 10 mM phosphate, pH 8.0 was circulated onto a Sepharose column that was previously immobilized with Aeromonas aminopeptidase. The volume of the reservoir is between 100 ml to 700 ml depending on the concentration of the protein. Typically, Ala-hGH is in 5–10 mg per ml. The flow rate is between 2–4 ml per minute. This was performed at 20° C. for about 24 hours. The reaction was monitored by RP-HPLC. Cleavage efficiency was confirmed by mass spectrometry and N-terminal sequencing. Finished product was then further purified by ion exchange chromatography.

Table 2 illustrates the effect of flow rate on cleavage of Ala-hGH using immobilized AAP at 28 ° C. in recirculation mode. Shorter residence times, were generally associated with higher levels of uncleaved substrate.

TABLE 2

Circulation mode cleavage of Ala-hGH at 28° C.

| Flow rate (ml/min) | Flow rate (ml/hr) | Residence time (hrs) | % Non-cleaved* Trypsin digest |
|---|---|---|---|
| 0.119 | 7.14 | 7.14 | 0.92 |
| 0.167 | 10.03 | 5.08 | 1.18 |
| 0.262 | 15.72 | 3.24 | 2.11 |
| 0.400 | 24.00 | 2.13 | (1.65) |
| 0.573 | 34.38 | 1.48 | 2.26 |
| 0.867 | 52.02 | 0.98 | 2.17 |

*The experiment was performed at 28° C. in a column volume of 51 ml using 10 mM phosphate, pH8 as buffer using Ala-hGH: 8 mg/ml (HPLC).

Table 3 illustrates the effect of flow rate on cleavage of Ala-hGH using immobilized AAP at 20° C. in recirculation mode. Shorter residence times, directly correlated with higher levels of uncleaved substrate.

TABLE 3

Circulation mode cleavage of Ala-hGH at 20° C.

| Flow rate (ml/min) | Flow rate (ml/hr) | Residence time (hrs) | % Non-cleaved Trypsin digest |
|---|---|---|---|
| 0.117 | 7.02 | 7.26 | 1.34 |
| 0.164 | 9.84 | 5.18 | 2.12 |
| 0.255 | 15.27 | 3.34 | 3.83 |
| 0.404 | 24.21 | 2.11 | 4.54 |
| 0.567 | 34.87 | 1.46 | 5.20 |
| 0.849 | 50.94 | 1.00 | 14.99 |
| 1.23 | 73.64 | 0.69 | 21.27 |

The experiment was performed at 20° C. with a column volume of 51 ml, in 10 mM phosphate buffer, pH 8 using Ala-hGH: 8 mg/ml (HPLC).
*Approximately 1% are the cysteine adduct that co-eluted with the non-cleaved Ala-T1 peptide.

Flow-through Mode:

Ala-hGH (8 mg/ml concentration) in 10 mM borate, pH 9.5 or 10 mM phosphate, pH 8.0 was introduced onto a Sepharose column (column volume is 50 ml) that was previously immobilized with Aeromonas aminopeptidase. The flow was adjusted to 15 ml per hour so the residence time to be around 3 hours. Cleavage efficiency was confirmed by RP-HPLC, tryptic digest, mass spectrometry or N-terminal sequencing. The eluent was collected and processed for downstream chromatographic purification.

Table 4 illustrates the effect of flow rate on cleavage of Ala-hGH using immobilized AAP at 28 ° C. in flow-through mode. Most of the Ala-hGH was processed by AAP under these conditions.

TABLE 4

Flow-through mode cleavage at 28° C.

| Flow rate (ml/hr) | Residence time (hrs) | % non-cleaved* (based on Trypsin digest) |
|---|---|---|
| 7.14 | 7.14 | <0.92 |
| 10.03 | 5.08 | <1.18 |
| 15.72 | 3.24 | <2.11 |
| 24 | 2.13 | NA |
| 34.4 | 1.48 | <2.26 |
| 52.02 | 0.98 | NA |

*All the tryptic data are based on the combination of uncleaved Ala-hGH and a process impurity. The real value of the uncleaved Ala-hGH is estimated about 50% of the reported values.

EXAMPLE 4

Comparison of Steady-flow and Continuous-flow Cleavage Processes

Column mode cleavage can be done at a much lower flow rate in one pass as long as the overall residence time is met. Run #1 was a typical run in the re-circulating mode. Run #2 was operated at 1/10 of the flow rate of run #1. However, run #2 was performed at 176 min per pass as compared to 18 min per pass for run #1. The overall residence time for both runs is about the same, ~180 minutes. The two modes are illustrated in FIG. 4.

TABLE 5

Effect of flow rate on activity

| run # | Column Volume, ml | Flow rate, ml/hr | Total passes | Residence time per pass | Residence time total contact time |
|---|---|---|---|---|---|
| 1 | 57 | 192 | 10 | 18 min | 180 min |
| 2 | 57 | 19.8 | 1 | 175 min | 175 min |

Table 6 illustrates the effect of the number of passes on cleavage of Ala-hGH using immobilized AAP at 28° C. in recirculation mode. Most of the Ala-hGH was processed by AAP under these conditions.

TABLE 6

Recirculation at 28° C. in phosphate buffer

| Time, hrs | # passes | % cleavage | Analyzed by |
|---|---|---|---|
| 2.92 | 1.06 | >93 | RP-HPLC |
| 5.73 | 2.08 | >96.1 | Tryptic map |
| 15.57 | 5.66 | >98.6 | Tryptic map |
| 17.73 | 6.45 | >98.6 | Tryptic map |
| 20.4 | 7.42 | >98.6 | Tryptic map |
| 23.4 | 8.8 | >98.8 | Tryptic map |
| 24.4 | 8.87 | >98.8 | Tryptic map |
| 39.7 | 14.44 | >99.2 | Tryptic map |

*[Ala-hGH] = 9.2 mg/ml; 500 ml load

Table 7 illustrates the effect of temperature and residence time on cleavage of Ala-hGH. A ten degree difference in temperature appears to affect the cleavage efficiency. A longer residence time may be required if a higher % cleavage is needed.

TABLE 7

Effect of temperature and residence time on steady-flow cleavage process:

| Run # | Temperature, ° C. | Flow rate, ml/hr | Residence time, min | % cleavage* |
|---|---|---|---|---|
| 1A | 20 | 0.28 | 182 | >98.5 |
| 1B | 30 | 0.28 | 182 | >99.1 |
| 2A | 20 | 0.51 | 100 | >95.8 |
| 2B | 30 | 0.51 | 100 | >98.3 |

*Cleavage products were analyzed by the peptide mapping method.

EXAMPLE 5

Enhancement of AAP Alanyl-processing Activity with Copper

The effects of substituting $Cu^{2+}$ or $Ni^{2+}$ for the native $Zn^{2+}$ catalytic cofactor of AAP were examined in the immobilized system for in vitro processing of Ala-hGH. This Cu-AAP can be prepared either directly from the AAP purification process step or be converted to the copper species by replacing the zinc counter metals that is present as in the commercial material. The conversion can be done either as the free enzyme or as the immobilized form.

Immobilized Cu-AAP from Zn-AAP Sepharose:

Cu-AAP was immobilized as described above. Resin slurry (sample A, 20 ml with 10 ml resin bed volume) was placed in a 250 ml sinter-glass funnel and drawn to near dryness using by vacuum. To this, 20 ml of 50 mM Tricine/50 mM KCl, pH 7.5 and 20 mM 1,10 phenanthroline were added and mixed for 20 minutes. The solution was removed and placed in fresh buffer containing 1,10-phenanthroline and mixed for another 2 hours. The buffer was removed and the resin slurry was washed with water and HEPES buffer, pH 7.5. The resulting resin was divided into two tubes each with a total volume of 12 ml. To B, 0.2 mM $CuCl_2$ in 50 mM HEPES, pH 7.5 was added, and to C, 0.2 mM $ZnCl_2$ in 50 mM HEPES, pH 7.5 was added. Both tubes were rocked gently for 3 hours. The slurries were washed extensively with water and stored in the desired buffer, such as borate, pH 9.6.

TABLE 8

Activity of metallo-modified AAP against Leu-pNA

| Samples | Metallo AAP | Activity unit/ml bed substrate: Leu-pNA |
|---|---|---|
| A (as is) | Zn-AAP | 8.94 |
| B | Zn-AAP | 8.59 |
| C | Cu-AAP | 5.47 |

The rate of Ala-hGH cleavage by Cu-AAP and Zn-AAP was compared in both batch and recirculating column modes. In the batch cleavage trial, 0.5 ml of a 1:1 slurry of each resin (B or C) was added to 2.056 ml of 10 mM borate buffer, pH 9.5 prior to the addition of Ala-hGH to a final concentration of 0.8 mg/ml. The reactions were followed over 24 hours by collection of samples that were quenched by filtering out the immobilized enzyme through a 0.45 μm filter. The filtrate was then analyzed by RP-HPLC to determine the fraction of Ala-hGH that had been cleaved.

In the recirculating column cleavage trial, 1 cm×5 cm columns were poured containing either the Cu-AAP resin (B) or the control AAP resin (B). These columns were equilibrated with 10 mM phosphate and 60 ml of 4.75 mg/ml Ala-hGH was recirculated through each of the columns at 2 CV per hour. Aliquots were collected and quenched at 3 hr, 6 hr, 18 hr and 28 hr for analysis as above.

FIG. 5 illustrates a time course of enhanced cleavage of Ala-hGH by Cu-AAP compared to Zn-AAP in batch mode. FIG. 6 illustrates a time course of Ala-hGH by Cu-AAP compared to Zn-AAP carried out in column recirculation mode.

Under all reaction conditions examined, $Cu^{2+}$-substituted AAP was the most active against Ala-hGH (FIGS. 5 and 6), even though the Cu-AAP is less active in the hydrolysis of the chromogenic substrates Leu-p-nitroanilide (pNA) (Table 8).

EXAMPLE 6

Detailed Structural Analysis of the Product Produced by Treatment of Ala-hGH with Aeromonas Aminopeptidase Purification of Ala-hGH Dissolution/Refold:

The inclusion body (IB) slurry was added to a pre-mixed solution containing 34.5 grams of sodium bicarbonate, 156 grams of amino-acid (e.g., sarcosine and/or glutamic acid) based detergent and 826 ml of water. The dissolved IB solution was held for 20 minutes at room temperature and cystine solution (100 mM, pH 10.0) was added. The solution was stirred for 15 hours at room temperature before cooling down to 4° C. The finished refold mixture was then concentrated to 4 liters, before being diafiltered against pH 10 water.

Acid Precipitation:

The diafiltered solution was diluted with pH 10.0 water to an Ala-hGH concentration of ~2.5 mg/ml. A 2% acetic acid solution was added using a peristaltic pump until the pH reached ~5.6 at 4–6° C. The acidified solution was stirred for an additional 30 minutes. The solution was then centrifuged at 6000 RPM for 30 minutes using a Sorvall RC5C centrifuge at 4° C. The supernatant was decanted and was then diafiltered against 10 mM sodium phosphate, pH 8.0. The protein concentration was then adjusted to 8 mg/ml.

Enzymatic Cleavage:

Aeromonas aminopeptidase was coupled onto resins such as Sepharose 4B resin via the cyanogen bromide chemistry (Hermanson, 1992). The activity of this immobilized enzyme was measured by the standard assay as suggested by Sigma using L-leucine-p-nitroanilide (Leu-pNA) as a substrate. Cold Ala-hGH solution (8 mg/ml) in 10 mM phosphate, pH 8.0 was passed through an immobilized enzyme column that was equipped with a water jacket and maintained at 25° C. The flow rate was adjusted to ~8 ml/hr to assure a sufficient contact time between Ala-hGH and the immobilized enzyme. The cleavage pool was then buffer exchanged against 3 M urea, 0.05 M acetic acid, pH 5.0 (buffer A) before loading onto the cation column.

Cation Column:

The cation load was introduced onto a 2.2×20 cm Amicon column packed with CM Sepharose resin. The total column load was 2.0 g of Ala-hGH. After loading, the column was washed with 1 CV (column volume) of buffer A, then eluted with a salt gradient from 0–0.2 M NaCl over a total of 54 CVs. The flow rate was 4 CV/hour. Column eluent was collected in 0.2 CV fractions and the eluent was monitored with a Gilson holochrome detector at 280 nm. Fractions were analyzed by cation exchange HPLC, and fractions with >95% purity were pooled.

Anion Column:

The cation pool was loaded onto a 1.6×20 cm Amicon column that was packed with Pharmacia Q-Sepharose resin. After loading, column was washed with one CV of Buffer A. A 40 CV linear gradient of 0–0.15 M NaCl in 0.05 M Tris-Cl pH 7.5 was done. The column eluent was collected as above. Fractions were analyzed by anion exchange HPLC and fractions with >98% purity were pooled.

Structural Analysis of the Cleavage Products

The most convenient method for the analysis of a cleavage reaction is the RP-HPLC method. However, the only reliable quantitative analysis is the peptide digest method. In this method, the detection limit for Ala-T1 is 0.25%.

Amino Acid Analysis:

After the cleavage reaction, the solution was centrifuged using a Centricon with 10 kDa molecular weight cut-off membrane. The alanine concentration in the filtrate can be measured by an amino acid analyzer. The degree of cleavage can then be calculated by the amount of alanine released from the reaction. In addition, any other amino acid detected should be an indication of non-specific cleavage.

RP-HPLC Analysis:

An isocratic method utilizing N-propanol (NPA)/0.25M phosphate pH 6.5 (26:74) as the mobile phase was used for analyzing Ala-hGH and hGH on a Vydac 214ATP54 column. The separation was carried out at 40° C. This method was used mainly in monitoring the formation of hGH via enzymatic cleavage of Ala-hGH. It also served as a secondary tool in deciding which fractions to collect from a cation exchange column.

FIGS. 7 and 8 illustrate typical HPLC profiles. FIG. 7 illustrates HPLC profiles of Ala-hGH before cleavage with AAP, incomplete cleavage, and after the reaction is complete. FIG. 8 illustrates the HPLC profile of hGH prepared by treating Ala-hGH with AAP, and two commercial preparations of hGH (Humatrope and Zomacton).

Peptide Mapping using Trypsin:

A solution of hGH was adjusted to pH 7.5 with 0.5 N NaOH. This solution was diluted with Tris base (50 mM, pH 7.5) so that the final concentration was 2 mg/ml. Then 15 mL of trypsin solution (1 mg/mL in 50 mM Tris base, pH 7.5) was added. The sample was mixed and incubated at 37 ° C. for 4 hrs, then quenched with 50 mL of HCl (0.5 M). An aliquot of the digested solution was injected on RP-HPLC and peptides were resolved by an acetonitrile gradient with 0.1% TFA.

This method provides information for the assessment of the primary and secondary structural integrity of hGH. Most importantly, this is the best method for analyzing trace level of un-cleaved Ala-hGH in the cleavage reaction and in the final product. The only difference between the tryptic digests of hGH and Ala-hGH is the N-terminal octa-peptide, T1 vs. Ala-T1. These two peptides are baseline resolved using an isocratic RP-HPLC method.

T1: FPTIPLSR (SEQ ID NO: 6)

Ala-T1: AFPTIPLSR (SEQ ID NO: 7)

FIGS. 9–12 illustrate typical tryptic map profiles. FIG. 9 illustrates the profile tracings illustrating the difference in mobility of the Ala-T1 peptide compared to the T1 peptide. FIG. 10 shows a vertically expanded profile tracing, illustrating the differences in peak areas under the elution positions for Ala-T1 and T1. FIG. 11 illustrates the tryptic maps of hGH purified after treatment of Ala-hGH with AAP compared to tryptic maps of hGH from commercial sources (Humatrope and Zomacton). FIG. 12 shows a vertically expanded profile tracing illustrating the presence or absence of Ala-T1 in a crude preparation of hGH, the final bulk preparation of hGH, and hGH from two commercial sources (Humatrope and Zomacton).

Electrospray Mass Spectrometry (ES/MS):

Measurement is based on the peak intensity for hGH (22,125) and Ala-hGH (22,195). The presence of other peaks is indicative of non-specific enzymatic cleavage.

FIG. 13 illustrates ES/MS profiles of Ala-hGH before cleavage with AAP, incomplete cleavage, and after the reaction is complete. FIG. 8 illustrates the HPLC profile of hGH prepared by treating Ala-hGH with AAP, and two commercial preparations of hGH (Humatrope and Zomacton).

FIG. 14 illustrates a superimposed ES/MS profile of Ala-hGH and hGH (bottom panel) along with HPLC tracings of the final product resolved on RP-HPLC and SE-HPLC columns.

N-terminal Sequencing:

N-terminal protein sequencing was performed by standard methods. The relative amounts of Ala (present in Ala-hGH) and Phe (in hGH) as the N-terminal amino acid are indicative of the degree of cleavage. Internal cleavage can also be detected by N-terminal sequence analysis.

FIG. 15 illustrates tracings of the products released after cycle 1 and cycle 2 from an automated protein sequencer. Phenylalanine (18.3 min) is the only significant residue detected after one cycle (left panel). Proline (14.2 min) is the only significant residue detected in cycle 2. The amount of alanine (*) is negligible in both cycles, indicating lack of N-terminal alanine residues in the final purified product.

EXAMPLE 7

In-vitro Processing of Alanyl Tissue Factor Pathway Inhibitor (Ala-TFPI) using Amino Peptidase Ala-TFPI, isolated from *E. coli* (U.S. Pat. No. 5,212,091), can be processed to TFPI using AAP in solution. Properly refolded Ala-TFPI is adjusted to 0.5–3 mg per ml concentration in 10 mM phosphate, pH 8.0 or 10 mM borate, pH 9.5. To this, Aeromonas aminopeptidase is added to a concentration of 3 units per ml and the reaction is allowed to proceed for 24–36 hours at ambient temperature or for a shorter time at 37° C. The progress of the cleavage reaction can be monitored by HPLC method or by amino acid analysis of the release of alanine from Ala-TFPI. At the end of reaction, the solution is quenched by adding 2% acetic acid (1:1.5 dilution w/w). The degree of cleavage is determined by HPLC analysis of the tryptic peptide fragments and by ES/MS of the isolated product.

Ala-TFPI can also be processed to TFPI using an immobilized AAP as described above. The degree of cleavage is determined by HPLC analysis of the tryptic peptide fragments and by ES/MS of the isolated product.

All references, patents, or patent applications cited herein are incorporated by reference in their entirety, as if written herein.

What is claimed is:

1. A method for removing an alanyl residue from the N-terminal region of a polypeptide, the method comprising expressing a polypeptide having an alanyl residue in the N-terminal region of the polypeptide, forming a solution containing the expressed polypeptide and contacting the solution with immobilized *Aeromonas proteolytica* aminopeptidase to cleave the alanyl residue from at least about 48% of the polypeptide molecules in the solution.

2. The method of claim 1, wherein the alanyl residue is non-native to the polypeptide.

3. The method of claim 2, wherein the alanyl residue is cleaved to yield a polypeptide having a native amino acid sequence.

4. The method of claim 3, wherein the polypeptide is expressed in an expression system selected from the group consisting of a mammalian, a bacterial, and an insect expression system.

5. The method of claim 4, wherein the polypeptide is a human polypeptide.

6. The method of claim 3, wherein the polypeptide is selected from the group consisting of human growth hormone (HGH), bovine somatotropin (bST), porcine somatotropin, (pST), and human tissue factor pathway inhibitor (TFPI).

7. The method of claim 3, wherein the contacting is carried out at a pH from about pH 7 to about pH 11.

8. The method of claim 1, wherein the polypeptide is a human polypeptide.

9. The method of claim 1, wherein the aminopeptidase is immobilized on a solid support selected from the group consisting of chromatography resin, chromatography surface, or chromatography gel.

10. The method of claim 1, wherein the polypeptide that is contacted with the aminopeptidase is recirculated such that the polypeptide is contacted with the aminopeptidase at least one additional time.

11. The method of claim 10, wherein the contacting occurs at a temperature from about 20° C. to about 40° C.

12. The method of claim 1, wherein a $Zn^{2+}$ native catalytic cofactor of the aminopeptidase is replaced with a cation selected from the group consisting of $Cu^{2+}$ and $Ni^{2+}$.

13. The method of claim 1, wherein the alanyl residue is cleaved from at least about 65% of the polypeptide molecules in the solution.

14. The method of claim 1, wherein the alanyl residue is cleaved from at least about 75% of the polypeptide molecules in the solution.

15. The method of claim 1, wherein the alanyl residue is cleaved from at least about 85% of the polypeptide molecules in the solution.

16. The method of claim 1, wherein the alanyl residue is cleaved from at least about 96% of the polypeptide molecules in the solution.

17. A method for removing an N-terminal alanyl residue from a polypeptide, the method comprising expressing a polypeptide having an N-terminal alanyl residue, forming a solution containing the expressed polypeptide and contacting the solution with immobilized *Aeromonas proteolytica* aminopeptidase to cleave the N-terminal alanyl residue from at least about 48% of the polypeptide molecules in the solution.

18. The method of claim 17, wherein the alanyl residue is non-native to the polypeptide.

19. The method of claim 18, wherein the alanyl residue is cleaved to yield a polypeptide having a native amino acid sequence.

20. The method of claim 19, wherein the polypeptide is expressed in an expression system selected from the group consisting of a mammalian, a bacterial, and an insect expression system.

21. The method of claim 20, wherein the polypeptide is a human polypeptide.

22. The method of claim 19, wherein the polypeptide is selected from the group consisting of human growth hormone (HGH), bovine somatotropin (bST), porcine somatotropin, (pST), and human tissue factor pathway inhibitor (TFPI).

23. The method of claim 19, wherein the contacting is carried out at a pH from about pH 7 to about pH 11.

24. The method of claim 17, wherein the polypeptide is a human polypeptide.

25. The method of claim 17, wherein the aminopeptidase is immobilized on a solid support selected from the group consisting of chromatography resin, chromatography surface, or chromatography gel.

26. The method of claim 17, wherein the polypeptide that is contacted with the aminopeptidase is recirculated such that the polypeptide is contacted with the aminopeptidase at least one additional time.

27. The method of claim 26, wherein the contacting occurs at a temperature from about 20° C. to about 40° C.

28. The method of claim 17, wherein a $Zn^{2+}$ native catalytic cofactor of the aminopeptidase is replaced with a cation selected from the group consisting of $Cu^{2+}$ and $Ni^{2+}$.

29. The method of claim 17, wherein the alanyl residue is cleaved from at least about 65% of the polypeptide molecules in the solution.

30. The method of claim 17, wherein the alanyl residue is cleaved from at least about 75% of the polypeptide molecules in the solution.

31. The method of claim 17, wherein the alanyl residue is cleaved from at least about 85% of the polypeptide molecules in the solution.

32. The method of claim 17, wherein the alanyl residue is cleaved from at least about 96% of the polypeptide molecules in the solution.

33. A method for removing an N-terminal alanyl residue from a recombinantly expressed polypeptide having an N-terminal alanyl residue, the method comprising forming a solution containing the expressed polypeptide and contacting the solution with immobilized *Aeromonas proteolytica* aminopeptidase to cleave the N-terminal alanyl residue from at least about 48% of the polypeptide molecules in the solution.

34. The method of claim 33, wherein the alanyl residue is non-native to the polypeptide.

35. The method of claim 34, wherein the alanyl residue is cleaved to yield a polypeptide having a native amino acid sequence.

36. The method of claim 35, wherein the polypeptide is expressed in an expression system selected from the group consisting of a mammalian, a bacterial, and an insect expression system.

37. The method of claim 36, wherein the polypeptide is a human polypeptide.

38. The method of claim 35, wherein the polypeptide is selected from the group consisting of human growth hormone (HGH), bovine somatotropin (bST), porcine somatotropin, (pST), and human tissue factor pathway inhibitor (TFPI).

39. The method of claim 35, wherein the contacting is carried out at a pH from about pH 7 to about pH 11.

40. The method of claim 33, wherein the polypeptide is a human polypeptide.

41. The method of claim 33, wherein the aminopeptidase is immobilized on a solid support selected from the group consisting of chromatography resin, chromatography surface, or chromatography gel.

42. The method of claim 33, wherein the polypeptide that is contacted with the aminopeptidase is recirculated such that the polypeptide is contacted with the aminopeptidase at least one additional time.

43. The method of claim 42, wherein the contacting occurs at a temperature from about 20° C. to about 40° C.

44. The method of claim 33, wherein a $Zn^{2+}$ native catalytic cofactor of the aminopeptidase is replaced with a cation selected from the group consisting of $Cu^{2+}$ and $Ni^{2+}$.

45. The method of claim 33, wherein the alanyl residue is cleaved from at least about 65% of the polypeptide molecules in the solution.

46. The method of claim 33, wherein the alanyl residue is cleaved from at least about 75% of the polypeptide molecules in the solution.

47. The method of claim 33, wherein the alanyl residue is cleaved from at least about 85% of the polypeptide molecules in the solution.

48. The method of claim 33, wherein the alanyl residue is cleaved from at least about 96% of the polypeptide molecules in the solution.

* * * * *

SEQUENCE LISTING

```
<160> NUMBER OF SEQ ID NOS: 7

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide to test substrate
      specificity of E. coli methionine aminopeptidase

<400> SEQUENCE: 1

Met Ala Pro Thr Ser Ser Ser Thr Lys Lys Thr Gln Leu
 1               5                  10

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide to test substrate
      specificity of E. coli methionine aminopeptidase

<400> SEQUENCE: 2

Met Pro Thr Ser Ser Ser Thr Lys Lys Gln Cys
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Synthetic peptide to test substrate
      specificity of E. coli methionine aminopeptidase

<400> SEQUENCE: 3

Leu Ala Pro Thr Ser Ser Ser Thr Lys Lys Thr Gln Leu
 1               5                  10

<210> SEQ ID NO 4
<211> LENGTH: 12
<212> TYPE: PRT
<213> ORGANISM: Artificial Sequence
```

-continued

```
<220> FEATURE:
<223> OTHER INFORMATION: Synthetic peptide to test substrate
      specificity of E. coli methionine aminopeptidase

<400> SEQUENCE: 4

Ala Pro Thr Ser Ser Ser Thr Lys Lys Thr Gln Leu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide to test substrate
      specificity of E. coli methionine aminopeptidase

<400> SEQUENCE: 5

Pro Thr Ser Ser Ser Thr Lys Lys Gln Cys
1               5                   10

<210> SEQ ID NO 6
<211> LENGTH: 8
<212> TYPE: PRT
<213> ORGANISM: Artificial Sequence
<220> FEATURE:
<223> OTHER INFORMATION: T1 is the N-terminal tryptic peptide of native
      human hGH

<400> SEQUENCE: 6

Phe Pro Thr Ile Pro Leu Ser Arg
1               5

<210> SEQ ID NO 7
<211> LENGTH: 9
<212> TYPE: PRT
<213> ORGANISM: Artificial Sequence
<220> FEATURE:
<223> OTHER INFORMATION: Ala-T1 is the N-terminal tryptic peptide of
      Ala-hGH

<400> SEQUENCE: 7

Ala Phe Pro Thr Ile Pro Leu Ser Arg
1               5
```